(12) United States Patent
Chong

(10) Patent No.: US 10,548,520 B2
(45) Date of Patent: Feb. 4, 2020

(54) NON-INVASIVE OPTICAL MEASUREMENT OF BLOOD ANALYTE

(71) Applicant: SANTEC CORPORATION, Komaki, Aichi (JP)

(72) Inventor: Changho Chong, Los Altos, CA (US)

(73) Assignee: SANTEC CORPORATION, Komaki (JP)

(*) Notice: Subject to any disclaimer, the term of this patent is extended or adjusted under 35 U.S.C. 154(b) by 581 days.

(21) Appl. No.: 15/086,520

(22) Filed: Mar. 31, 2016

(65) Prior Publication Data

US 2016/0287154 A1 Oct. 6, 2016

Related U.S. Application Data

(60) Provisional application No. 62/141,402, filed on Apr. 1, 2015.

(51) Int. Cl.
A61B 5/1455 (2006.01)
A61B 5/145 (2006.01)
A61B 3/10 (2006.01)
A61B 5/01 (2006.01)
A61B 5/1495 (2006.01)

(52) U.S. Cl.
CPC .......... A61B 5/14555 (2013.01); A61B 3/102 (2013.01); A61B 5/14532 (2013.01); A61B 5/14546 (2013.01); A61B 5/01 (2013.01); A61B 5/1495 (2013.01)

(58) Field of Classification Search
CPC ... A61B 5/14555; A61B 3/102; A61B 3/1233; A61B 5/0066; A61B 5/14532; A61B 5/14546; A61B 5/01; A61B 5/1075; A61B 5/1495; A61B 5/6821

USPC ........................................................ 600/318
See application file for complete search history.

(56) References Cited

U.S. PATENT DOCUMENTS

| 4,466,699 A | 8/1984 | Droessler et al. |
| 5,022,745 A | 6/1991 | Zayhowski et al. |
| 5,319,668 A | 6/1994 | Luecke |
| 5,372,135 A | 12/1994 | Mendelson et al. |
| 5,430,574 A | 7/1995 | Tehrani |
| 5,537,162 A | 7/1996 | Hellmuth et al. |
| 5,561,523 A | 10/1996 | Blomberg et al. |
| 5,979,760 A | 11/1999 | Freyman et al. |

(Continued)

FOREIGN PATENT DOCUMENTS

| DE | 10 2011 114 797 A1 | 4/2013 |
| JP | 2006-202543 A | 8/2006 |

(Continued)

OTHER PUBLICATIONS

Poddar et al, "Non-invasive Glucose Monitoring Techniques-A Review of Current Trends", Oct. 31, 2008, pp. 1-47.*

(Continued)

Primary Examiner — Eric F Winakur
(74) Attorney, Agent, or Firm — Foley & Lardner LLP

(57) ABSTRACT

Methods and devices for accurate noninvasive measurement of blood analyte concentrations are disclosed. In an example process, optical properties of a blood vessel proximate to the surface of an exposed body part, for example, the sclera or the backside of the eyelid, is measured. Analyte concentrations are determined based on the measured optical properties.

19 Claims, 13 Drawing Sheets

(56) References Cited

U.S. PATENT DOCUMENTS

| | | | |
|---|---|---|---|
| 5,982,963 A | 11/1999 | Feng et al. | |
| 6,070,093 A * | 5/2000 | Oosta | A61B 5/0095 356/39 |
| 6,111,645 A | 8/2000 | Tearney et al. | |
| 6,134,003 A | 10/2000 | Tearney et al. | |
| 6,160,826 A | 12/2000 | Swanson et al. | |
| 6,275,718 B1 | 8/2001 | Lempert | |
| 6,282,011 B1 | 8/2001 | Tearney et al. | |
| 6,373,632 B1 | 4/2002 | Flanders | |
| 6,421,164 B2 | 7/2002 | Tearney et al. | |
| 6,485,413 B1 | 11/2002 | Boppart et al. | |
| 6,501,551 B1 | 12/2002 | Tearney et al. | |
| 6,556,853 B1 | 4/2003 | Cabib et al. | |
| 6,564,087 B1 | 5/2003 | Pitris et al. | |
| 6,725,073 B1 * | 4/2004 | Motamedi | A61B 5/0066 600/316 |
| 7,099,358 B1 | 8/2006 | Chong | |
| 7,231,243 B2 | 6/2007 | Tearney et al. | |
| 7,323,680 B2 | 1/2008 | Chong | |
| 7,324,214 B2 | 1/2008 | De Groot et al. | |
| 7,352,783 B2 | 4/2008 | Chong | |
| 7,382,809 B2 | 6/2008 | Chong et al. | |
| 7,388,891 B2 | 6/2008 | Uehara et al. | |
| 7,400,410 B2 | 7/2008 | Baker et al. | |
| 7,414,779 B2 | 8/2008 | Huber et al. | |
| 7,428,057 B2 | 9/2008 | De Lega et al. | |
| 7,489,713 B2 | 2/2009 | Chong et al. | |
| 7,701,588 B2 | 4/2010 | Chong | |
| 7,725,169 B2 | 5/2010 | Boppart et al. | |
| 7,835,010 B2 | 11/2010 | Morosawa et al. | |
| 7,865,231 B2 | 1/2011 | Tearney et al. | |
| 7,869,057 B2 | 1/2011 | De Groot | |
| 7,884,945 B2 | 2/2011 | Srinivasan et al. | |
| 7,961,312 B2 | 6/2011 | Lipson et al. | |
| 8,036,727 B2 * | 10/2011 | Schurman | A61B 5/0066 600/322 |
| 8,115,934 B2 | 2/2012 | Boppart et al. | |
| 8,315,282 B2 | 11/2012 | Huber et al. | |
| 8,405,834 B2 | 3/2013 | Srinivasan et al. | |
| 8,427,649 B2 | 4/2013 | Hays | |
| 8,500,279 B2 | 8/2013 | Everett et al. | |
| 8,625,104 B2 | 1/2014 | Izatt et al. | |
| 8,690,328 B1 | 4/2014 | Chong | |
| 8,690,330 B2 | 4/2014 | Hacker et al. | |
| 9,163,930 B2 | 10/2015 | Buckland et al. | |
| 9,335,154 B2 | 5/2016 | Wax et al. | |
| 9,851,433 B2 | 12/2017 | Sebastian | |
| 2001/0034478 A1 | 10/2001 | Lambert et al. | |
| 2002/0163948 A1 | 11/2002 | Yoshida et al. | |
| 2004/0036838 A1 | 2/2004 | Podoleanu et al. | |
| 2005/0171438 A1 | 8/2005 | Chen et al. | |
| 2005/0201432 A1 | 9/2005 | Uehara et al. | |
| 2005/0213103 A1 | 9/2005 | Everett et al. | |
| 2006/0105209 A1 | 5/2006 | Thyroff et al. | |
| 2006/0109872 A1 | 5/2006 | Sanders | |
| 2006/0215713 A1 | 9/2006 | Flanders et al. | |
| 2007/0040033 A1 | 2/2007 | Rosenberg | |
| 2007/0076217 A1 | 4/2007 | Baker et al. | |
| 2007/0081166 A1 | 4/2007 | Brown et al. | |
| 2007/0133647 A1 | 6/2007 | Daiber | |
| 2007/0141418 A1 | 6/2007 | Ota et al. | |
| 2007/0263226 A1 * | 11/2007 | Kurtz | A61B 5/0059 356/492 |
| 2007/0291277 A1 | 12/2007 | Everett et al. | |
| 2008/0097194 A1 | 4/2008 | Milner | |
| 2008/0269575 A1 | 10/2008 | Iddan | |
| 2009/0022181 A1 | 1/2009 | Atkins et al. | |
| 2009/0079993 A1 | 3/2009 | Yatagai et al. | |
| 2009/0103050 A1 | 4/2009 | Michaels et al. | |
| 2009/0169928 A1 | 7/2009 | Nishimura et al. | |
| 2009/0247853 A1 * | 10/2009 | Debreczeny | A61B 5/0059 600/328 |
| 2009/0268020 A1 | 10/2009 | Buckland et al. | |
| 2009/0290613 A1 | 11/2009 | Zheng et al. | |
| 2010/0110171 A1 | 5/2010 | Satake | |
| 2010/0157308 A1 | 6/2010 | Xie | |
| 2010/0246612 A1 | 9/2010 | Shimizu | |
| 2010/0253908 A1 | 10/2010 | Hammer et al. | |
| 2010/0284021 A1 | 11/2010 | Hacker | |
| 2011/0112385 A1 * | 5/2011 | Aalders | A61B 5/0059 600/322 |
| 2011/0228218 A1 | 9/2011 | Hauger et al. | |
| 2011/0235045 A1 | 9/2011 | Koerner | |
| 2011/0255054 A1 | 10/2011 | Hacker et al. | |
| 2011/0299034 A1 | 12/2011 | Walsh et al. | |
| 2012/0013849 A1 | 1/2012 | Podoleanu et al. | |
| 2012/0026466 A1 | 2/2012 | Zhou et al. | |
| 2012/0133950 A1 | 5/2012 | Suehira et al. | |
| 2012/0136259 A1 | 5/2012 | Milner et al. | |
| 2012/0188555 A1 | 7/2012 | Izatt et al. | |
| 2013/0265545 A1 | 10/2013 | Buckland et al. | |
| 2014/0051952 A1 | 2/2014 | Reichgott et al. | |
| 2014/0111774 A1 | 4/2014 | Komine | |
| 2014/0228681 A1 | 8/2014 | Jia et al. | |
| 2014/0268163 A1 * | 9/2014 | Milner | A61B 3/102 356/451 |
| 2014/0293290 A1 | 10/2014 | Kulkarni | |
| 2014/0336479 A1 * | 11/2014 | Ando | A61B 5/4041 600/310 |
| 2015/0223681 A1 | 8/2015 | Kuranov et al. | |
| 2015/0348287 A1 | 12/2015 | Yi et al. | |
| 2016/0178346 A1 | 6/2016 | Kulkarni | |
| 2017/0090031 A1 | 3/2017 | Bondy et al. | |
| 2018/0088236 A1 | 3/2018 | Eichenholz et al. | |
| 2018/0128594 A1 | 5/2018 | Lee et al. | |

FOREIGN PATENT DOCUMENTS

| | | |
|---|---|---|
| JP | 2008-188047 A | 8/2008 |
| JP | 2010-172538 A | 8/2010 |
| WO | WO 2012/075126 A2 | 6/2012 |
| WO | WO-2013/168149 A1 | 11/2013 |
| WO | WO-2015/121756 A2 | 8/2015 |
| WO | WO-2017/176901 A1 | 10/2017 |

OTHER PUBLICATIONS

Chopra et al., Topographical Thickness of the Skin in the Human Face, Aesthetic Surgery Journal, vol. 35(8), 2015, pp. 1007-1013.*

Chowdhury, Md Koushik et al., Challenges & Countermeasures in Optical Noninvasive Blood Glucose Detection, International Journal of Innovative Research in Science, Engineering and Technology vol. 2, Issue 1, Jan. 2013 (6 pages).

International Search Report and Written Opinion dated Aug. 26, 2015 for PCT/US15/32727 (8 pages).

Chong, et al. "Large Coherence Length Swept Source for Axial Length Measurement of the Eye," Applied Optics, vol. 48, Issue 10, Apr. 1, 2009, pp. D145-D150.

Dai, et al., "Optical coherence tomography for whole eye segment imaging," Optics Express, vol. 20, Issue 6, Mar. 12, 2012, pp. 6109-6115.

Dhalla, et al., "Simultaneous swept source optical coherence tomography of the anterior segment and retina using coherence revival," Optics Letters, 2012, vol. 37, No. 11, pp. 1883-1885.

Fainman, et al., "Nanophotonics for Information Systems," Information Optics and Photonics, T. Fournel and B. Javidi eds., Springer New York, Oct. 1, 2010, pp. 13-37.

Final Rejection Office Action on U.S. Appl. No. 14/641,200 dated Dec. 7, 2015 (13 pages).

Non-Final Rejection Office Action on U.S. Appl. No. 15/202,925 dated Jul. 27, 2017 (8 pages).

International Preliminary Report on Patentability and Written Opinion on International Application No. PCT/US2015/032727 dated Dec. 8, 2016 (7 pages).

International Preliminary Report on Patentability on International Application No. PCT/IB2015/000808 dated Aug. 4, 2016 (7 pages).

International Preliminary Report on Patentability on International Application No. PCT/US2015/019299 dated Sep. 22, 2016 (8 pages).

(56) References Cited

OTHER PUBLICATIONS

International Preliminary Report on Patentability on International Application No. PCT/US2015/032727 dated Dec. 8, 2016 (7 pages).
International Preliminary Report on Patentability on International Application No. PCT/US2016/035012 dated Dec. 14, 2017 (11 pages).
International Search Report and Written Opinion on International Application No. PCT/EP2009/00918 dated Apr. 6, 2010 (12 pages).
International Search Report and Written Opinion on International Application No. PCT/162015/000808 dated Oct. 20, 2015 (12 pages).
International Search Report and Written Opinion on International Application No. PCT/US2015/19299 dated Nov. 2, 2015(10 pages).
International Search Report and Written Opinion on International application No. PCT/US2016/035012 dated Aug. 18, 2016 (13 pages).
Jeong, et al., "Spectral-domain OCT with dual illumination and interlaced detection for simultaneous anterior segment and retina imaging," Optics Express, vol. 20, Issue 17, Aug. 13, 2012, pp. 19148-19159.
Jia, et al., "Split-Spectrum Amplitude-Decorrelation Angiography with Optical Coherence Tomography," Optics Express, vol. 20 No. 4, Feb. 9, 2012, pp. 4710-4725.
Lexer, et al., "Wavelength-tuning interferometry of intraocular distances," Applied Optics, vol. 36, Issue 25, Sep. 1, 1997, pp. 6548-6553.
Mariampillai, et al., "Speckle Variance Detection of Microvasculature Using Swept-Source Optical Coherence Tomography," Optics Letters, vol. 33 No. 13, Jul. 1, 2008, pp. 1530-1532.
Nankivil, et al., "Handheld, rapidly switchable, anterior/posterior segment swept source optical coherence tomography probe," Biomedical Optics Express, vol. 6, Issue 11, Nov. 1, 2015, pp. 4516-4528.
Non-Final Office Action on U.S. Appl. No. 14/641,200 dated Aug. 19, 2015 (12 pages).
Non-Final Rejection Office Action on U.S. Appl. No. 13/892,997 dated Sep. 12, 2013 (14 pages).
Non-Final Rejection Office Action on U.S. Appl. No. 14/601,945 dated Mar. 2, 2016 (13 pages).
Non-Final Rejection Office Action on U.S. Appl. No. 14/613,644 dated Jun. 8, 2016 (8 pages).
Non-Final Rejection Office Action on U.S. Appl. No. 14/641,200 dated Mar. 14, 2016 (13 pages).
Non-Final Rejection Office Action on U.S. Appl. No. 14/723,325 dated Dec. 7, 2017 (10 pages).
Notice of Allowance on U.S. Appl. No. 13/892,997 dated Dec. 6, 2013 (9 pages).
Notice of Allowance on U.S. Appl. No. 14/601,945 dated Sep. 13, 2016 (9 pages).
Notice of Allowance on U.S. Appl. No. 14/641,200 dated Jul. 12, 2016 (10 pages).
Ortiz, et al., "Corneal Topography From Spectral Optical Coherence Tomography (sOCT)," Biomedical Optics Express, vol. 2, No. 12, Dec. 1, 2011, pp. 3232-3247.
Poddar, et al., "Non-Invasive Glucose Monitoring Techniques: A Review and Current Trends," Oct. 31, 2008, pp. 1-47.
Sarlet, et al., "Wavelength and Mode Stabilization of Widely Tunable SG-DBR and SSG-DBR Lasers," IEEE Photonics Technology Letters, vol. 11, Issue 11, Nov. 1999, pp. 1351-1353.
Segawa, et al., "Semiconductor Double-Ring-Resonator-Coupled Tunable Laser for Wavelength Routing," IEEE Journal of Quantum Electronics, vol. 45, Issue 7, Jul. 2009, pp. 892-899.
Tayebati, et al., "Microelectromechanical tunable filter with stable half symmetric cavity," Electronics Letters, vol. 34, Issue 20, Oct. 1, 1998, pp. 1967-1968.
U.S. Office Action on U.S. Appl. No. 14/723,325 dated Nov. 18, 2016.
International Search Report and Written Opinion in PCT/US2019/027671 dated Jul. 1, 2019.

* cited by examiner

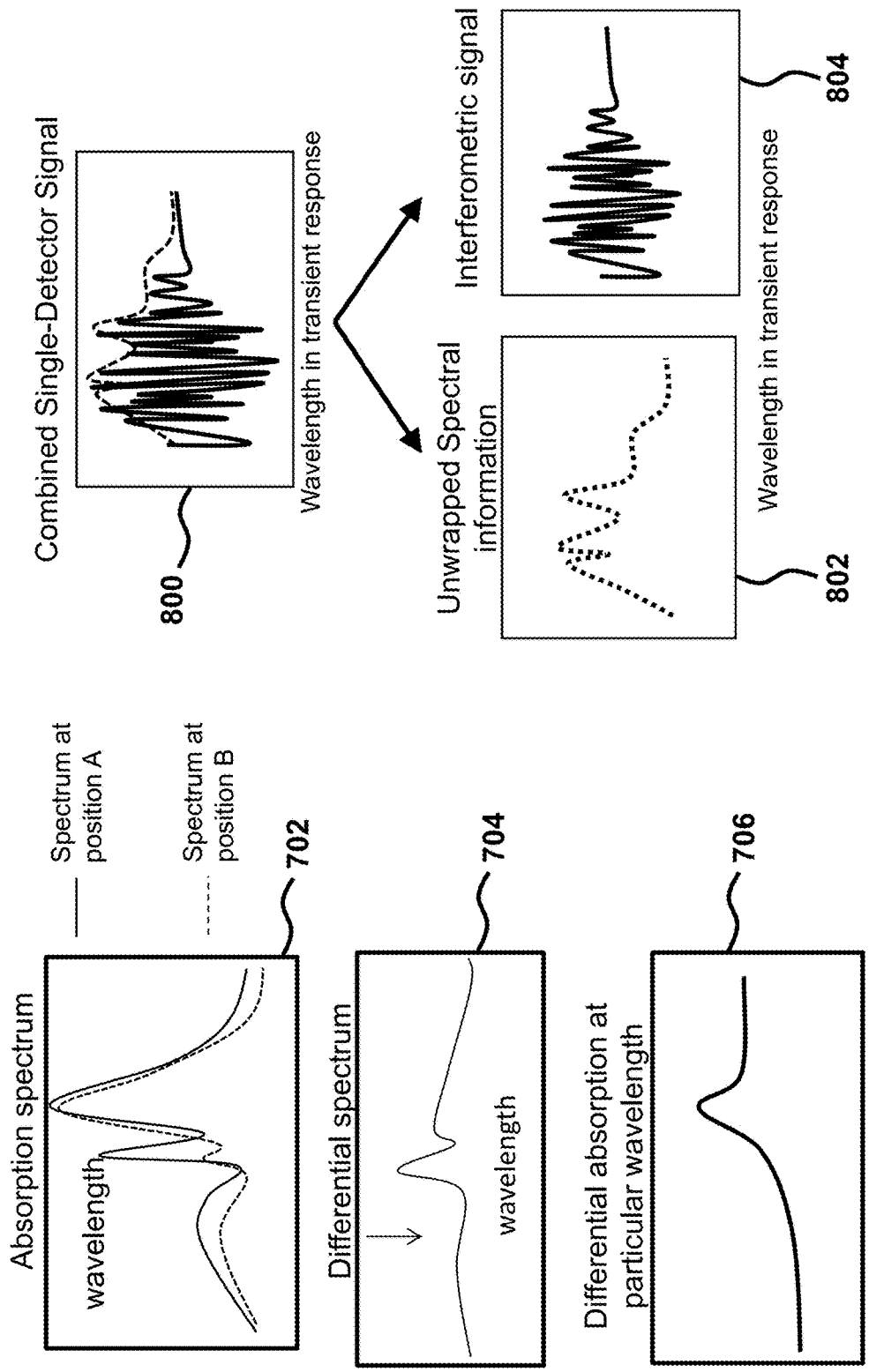

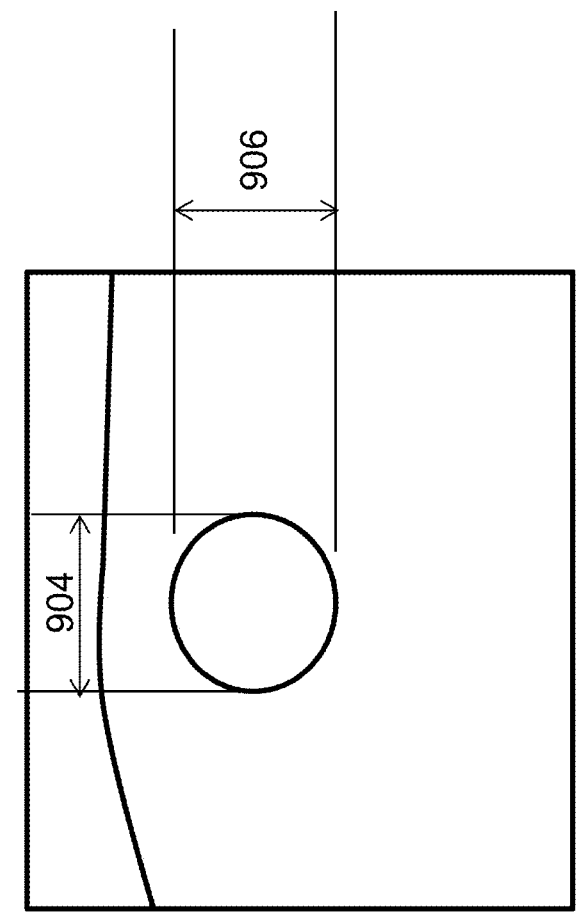
902:
Blood Vessel Idealized Model
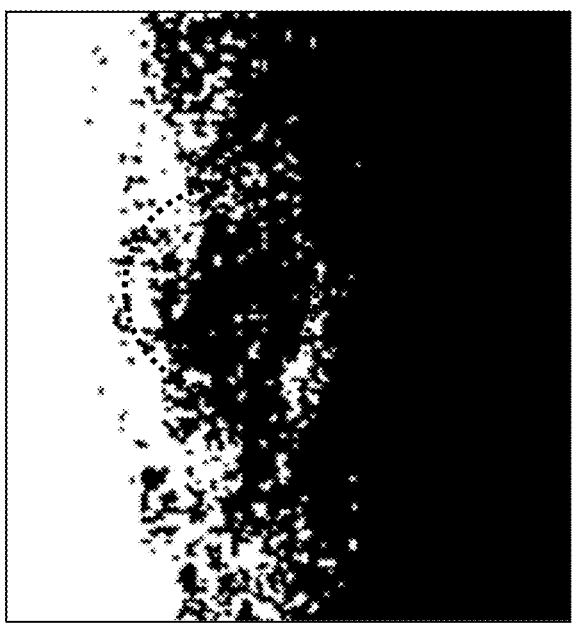
900:
Measured OCT image (with emphasized blood vessel profile)
Figure 9

NON-INVASIVE OPTICAL MEASUREMENT OF BLOOD ANALYTE

CROSS-REFERENCE TO RELATED APPLICATIONS

The present application claims priority under 35 U.S.C. § 119 to U.S. Provisional Patent Application No. 62/141,402, filed Apr. 1, 2015, the entire contents of which are incorporated by reference herein.

BACKGROUND

The following description is provided to assist the understanding of the reader. None of the information provided is admitted to be prior art.

The present disclosure is related to non-invasive optical measurement of blood analytes. The effective diagnosis and treatment of various diseases benefits from, and in some cases, requires determination of the concentration of certain blood constituents called analytes. For example, patients suffering from diabetes may need to regularly test their blood to determine glucose concentration. Conventionally, such tests require extraction of blood by puncturing the skin or blood vessel. This invasive technique discourages a patient's compliance with regular monitoring of blood glucose concentration. It would be beneficial to have a non-invasive technique for measuring the levels of analytes in blood.

SUMMARY

In one embodiment, an example noninvasive method is provided for accurately determining in vivo blood analyte concentrations. The method comprises receiving information associated with optical signals detected by a light detector. The optical signals are detected from an area illuminated by a light source. The area includes a blood vessel that is proximate to a surface of an exposed body part. The method also comprises determining a concentration of blood analyte based on the received information.

In another embodiment, an example non-invasive analyte detection device includes a light source, a light detector, and a processor. The light source is configured to illuminate an area that includes a blood vessel. The blood vessel is proximate to a surface of an exposed body part. The light detector is configured to detect optical signals from the area. The processor is configured to receive information associated with the detected optical signals from the light detector and to determine a concentration of a blood analyte based on the received information.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are; therefore, not to be considered limiting of its scope, the disclosure will be described with additional specificity and detail through use of the accompanying drawings.

FIGS. 7 and 8 Illustrate example received signals at various stages of example processes in accordance with an illustrative embodiment.

FIG. 9 depicts example signal and model for an optical coherence tomography (OCT) system according to an example embodiment.

DETAILED DESCRIPTION

Figure 1:
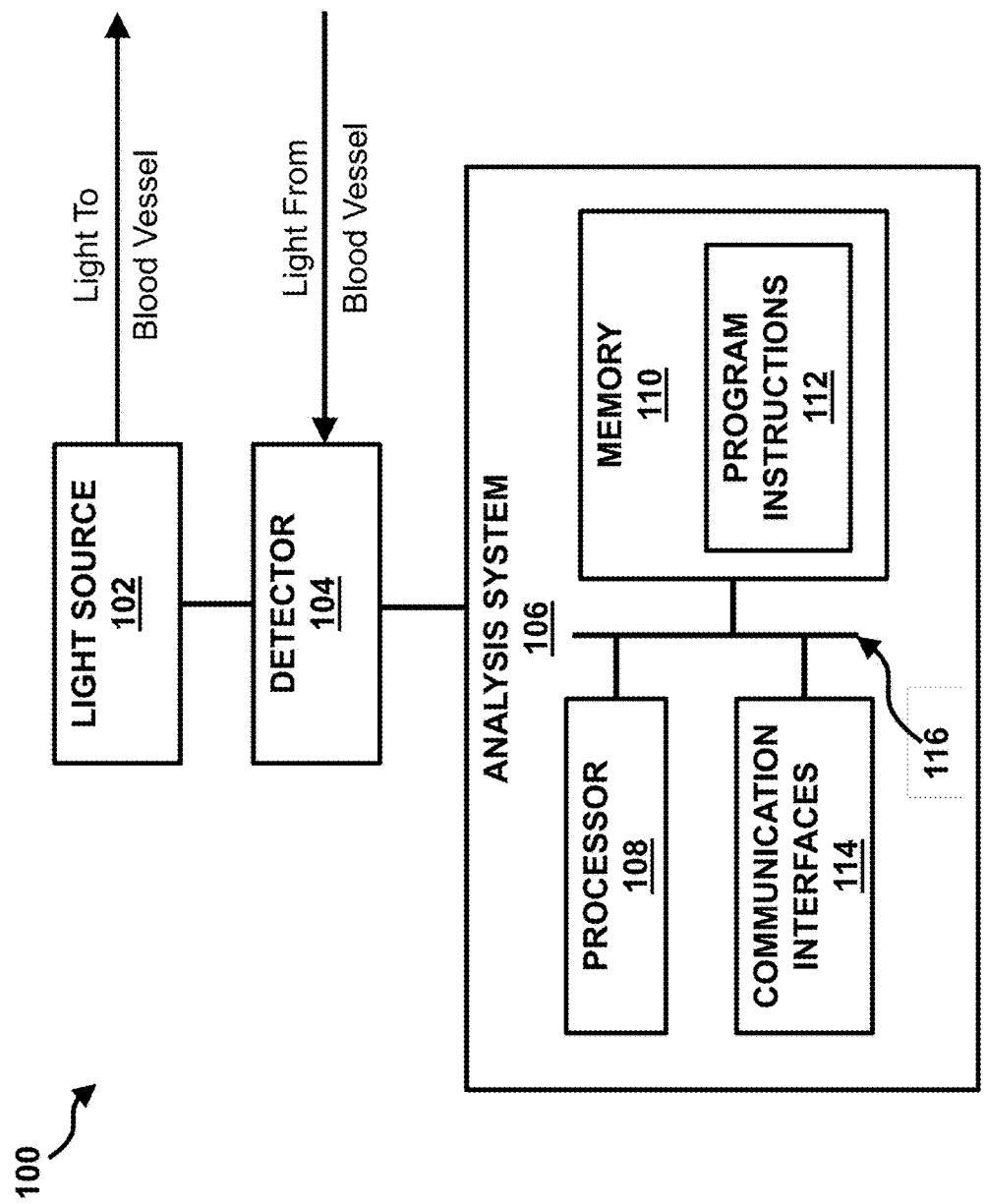
FIG. 1 is a block diagram showing elements of an example detection device in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Described herein are example methods and devices for facilitating non-contact detection of blood analyte concentrations. Although the example methods reference elements from the example devices (or similar structures that could be used in such devices), this is not intended to imply that the example devices and methods must be used together. Rather, the example methods may be carried out using any suitable devices, systems, or combination of systems and the described example devices may carry out procedures other than those outlined in the example methods.

Example Device and System Architecture

FIG. 1 is a block diagram illustrating elements of an example analyte detection device 100 in accordance with an illustrative embodiment that may be used in combination with the procedures described below or with other techniques. As shown in FIG. 1, device 100 includes a light source 102 that is configured to provide light to a blood vessel. Device 100 also includes a detector 104 configured to detect light reflecting from or transmitting through the blood vessel. Device 100 also includes an analysis system for analyzing the detected light characteristics and performing additional functions as described hereinafter. As shown in FIG. 1, analysis system 106 includes a processor 108, a processor-readable memory 110, and one or more communication interfaces 114, communicatively coupled through a system bus 116. As shown, analysis system 106 may store program instructions 112 in memory 110, in order to cause processor 108 to perform certain functions when program instructions 112 are executed.

Light source 102 may include any single type of light-producing element or a combination of elements that are capable of producing light. Configuration of light source 102 depends on the optical approaches employed to measure the blood analyte concentration. For example, when the method uses polarization rotation to measure blood analyte concentrations, light source 102 is configured to produce polarized light the polarization of which can be changed by the blood analyte of interest. When an optical coherence tomography (OCT) is used, light source 102 is configured to produce a coherence light, for example, a super luminescent light. When the method uses Raman spectroscopy, light source 102 is configured to produce laser light that can induce oscillation and rotation in molecules of the blood analyte of interest. When the method uses near infrared spectroscopy (NIR) or mid-infrared spectroscopy (MIR), light source 102 is configured to produce NIR light or MIR light including at least an absorption frequency associated with the blood analyte of interest.

The frequency range of the light provided by light source 102 also depends on the optical measurement approaches employed and the blood analyte of interest. For example, for the polarization rotation method, visible spectrum light (400-700 nm wavelength) may be used in the process. For the NIR spectroscopy method, the frequency range between 800 nm and 2300 nm in the wavelength may be used. In one embodiment of the OCT method, a first suitable spectrum range is 400 nm-2300 nm. In another embodiment, another suitable spectrum range is 800 nm-2300 nm. In still another embodiment, a spectrum of 800-1400 nm wavelength may be preferable. It should be appreciated that the above-mentioned frequency ranges are for examples only, not for limitation. It should also be appreciated that other example ranges are possible.

In some embodiments, it may be preferable for light source 102 to have a controllably tunable wavelength of emission. For example, light source 102 may be a tunable laser in which signals from a controller are capable of causing the laser to change its emission wavelength. Other tunable light sources are possible through various control signals and structures. In some cases, light source 102 may continuously transmit a wide spectrum of frequencies, and tunability may be achieved through adjusting filters placed in the optical path of the light source. In some cases, a tunable light source may be controlled in an automatic fashion. For example, a control circuit may cause the tunable light source to repeatedly sweep across a range of frequencies without requiring additional control input. In some cases, sweeping across a range of frequencies may provide a substantially continuous spectrum. In other cases, a swept-wavelength source may sweep in a stepped fashion from one particular frequency to another without traversing a broad range of frequencies between the stable points.

Figure 4:
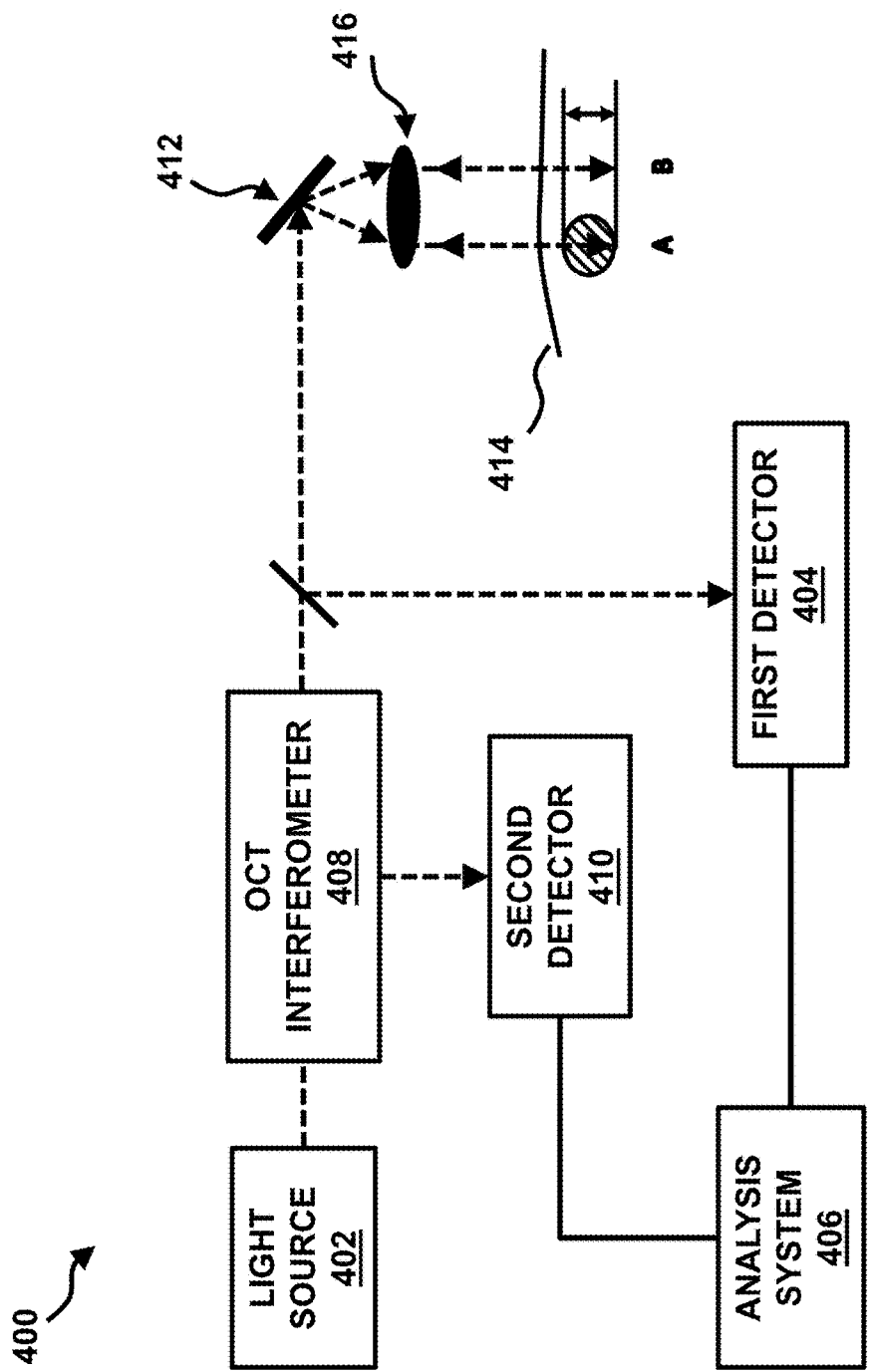
FIG. 4 is a simplified ray diagram illustrating an example detection device in use in accordance with an illustrative embodiment.
Figure 5:
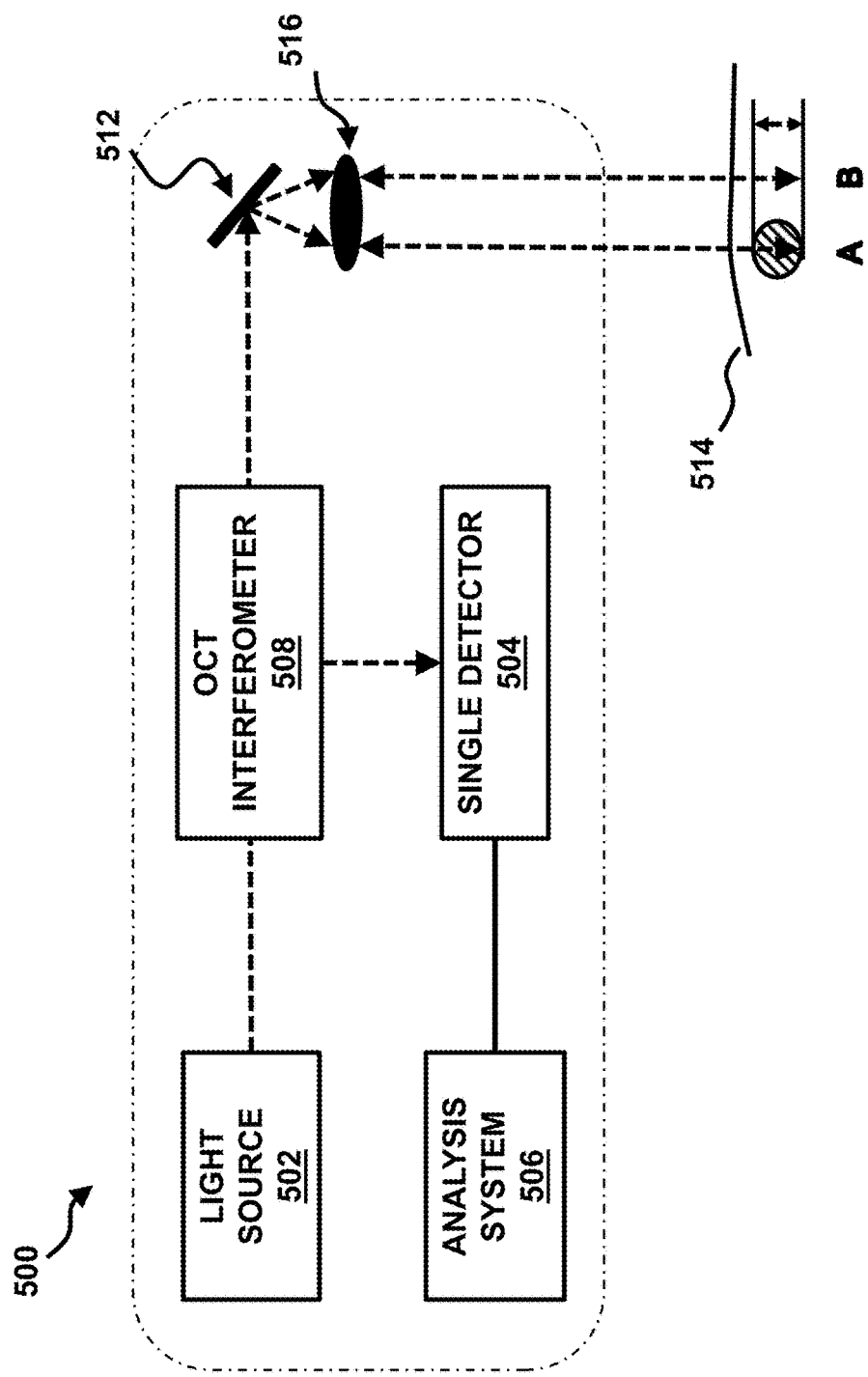
FIG. 5 is a simplified ray diagram illustrating an example detection device in use in accordance with an illustrative embodiment.

The wavelength of the light may also be controlled to correspond with the requirements of other optical components further down the optical path. For example, the output of interferometry systems, like those shown in FIGS. 4 and 5, is often affected by the particular frequency of the light being used. In such an example, the interferometry system may include tunable components that are in controllable communication with the controller of light source 102, so that the frequency changes in the input light are accompanied by corresponding changes in the interferometer.

Detector 104 may be configured specifically to work with light source 102. As with the above example of the interferometry system, detector 104 may be communicatively coupled to the light source 102, in order to maintain a synchronization of wavelength or other changes. In some cases, detector 104 may also be wavelength tunable. Indeed, if light source 102 is not wavelength tunable, a wavelength sweep in the system may be performed entirely by detector 104. In other cases, detector 104 may continuously detect a full spectrum of frequencies, without sweeping across them at any particular moment. As with light source 102, detector 104 may be tuned to detect near infrared wavelengths or other spectra capable of penetrating tissue.

Detector 104 may include any light-sensitive elements now known or forthcoming. In some cases, a single detector may be sufficient. In other cases, multiple detectors may detect different features (e.g., different wavelengths, different light polarization, light at different times steps, etc.). In still other cases, detector 104 may include spatial arrays of light-detection elements. In such an embodiment, the light signal received by detector 104 may represent a spatial image of the tissue area.

The size and shape of the scanned area may depend on the illumination profile of light source 102, the detection characteristics of detector 104, the characteristic of optical components in the beam paths (e.g., pinholes, lenses, mirrors, beam expanders), or a combination of these factors. In some example embodiments, the light propagating to the tissue area may be specifically generated or optically modified to have a spot size that is smaller than a diameter of the blood vessel in the tissue area. Such an embodiment may help to prevent illumination that is not meant to hit the blood vessel from scattering into blood vessel area. This technique may also provide focused illumination on only a blood vessel area when the system is attempting to illuminate the blood vessel area. In other embodiments, the detection system may be configured such that only light striking a small spot size detection area is received by detector 104. Such an embodiment provides similar effects as the embodiment with a smaller spot size of illumination. In order to provide such tissue area illumination or detector precision, the light going to the tissue area may be collimated and/or the polarization of the light may be controlled. In addition to the size and shape of the spot size, the depth of the light penetration/detection may be tailored to reach a particular depth in the tissue areas. In particular, the selected depth may be a depth associated with the blood vessel. The depth may be tailored by adjusting the angle of incidence (lower angle, less depth), the wavelength (wavelength farther from water/fat absorption levels, more depth), the spot size (smaller spot, more depth), or the intensity of the light (more intensity, more depth).

Figure 2:
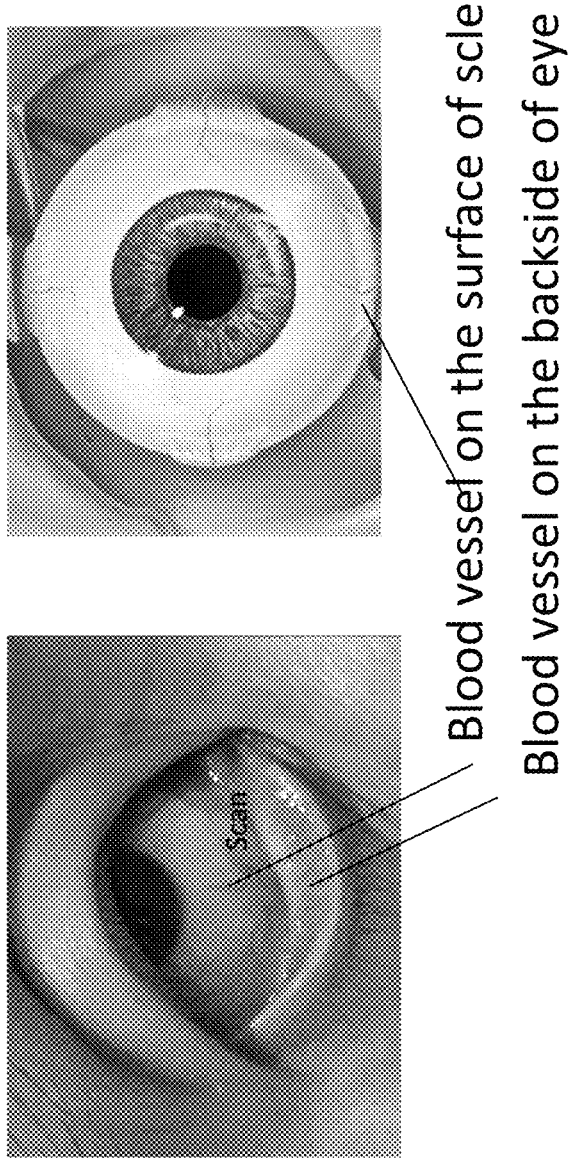
FIG. 2 illustrates blood vessels proximate to the surface of the sclera and blood vessels proximate to the surface of the backside of the eye lid.

In various embodiments, the blood vessels scanned by device 100 are proximate to the surface of an exposed body part. FIG. 2 shows example blood vessels that are proximate to the surface of an exposed body part. For example, blood vessels are located proximate to the surface of the sclera. In addition, blood vessels are located proximate to the surface of the backside of the eye lid. One of the challenges in effective non-invasive measurement of blood analyte concentration is the accuracy of the measurement. For example, in measuring optical absorption spectrum of glucose in blood, a weaker glucose spectrum is embedded in the relatively stronger spectrum of water, due to the large disparity in their respective concentrations. The glucose spectrum is also overlapped by the spectra of hemoglobin, protein, and fat, and affected by skin properties, perfusion, and interstitial fluid, rendering the measurement inaccurate.

Figure 3:
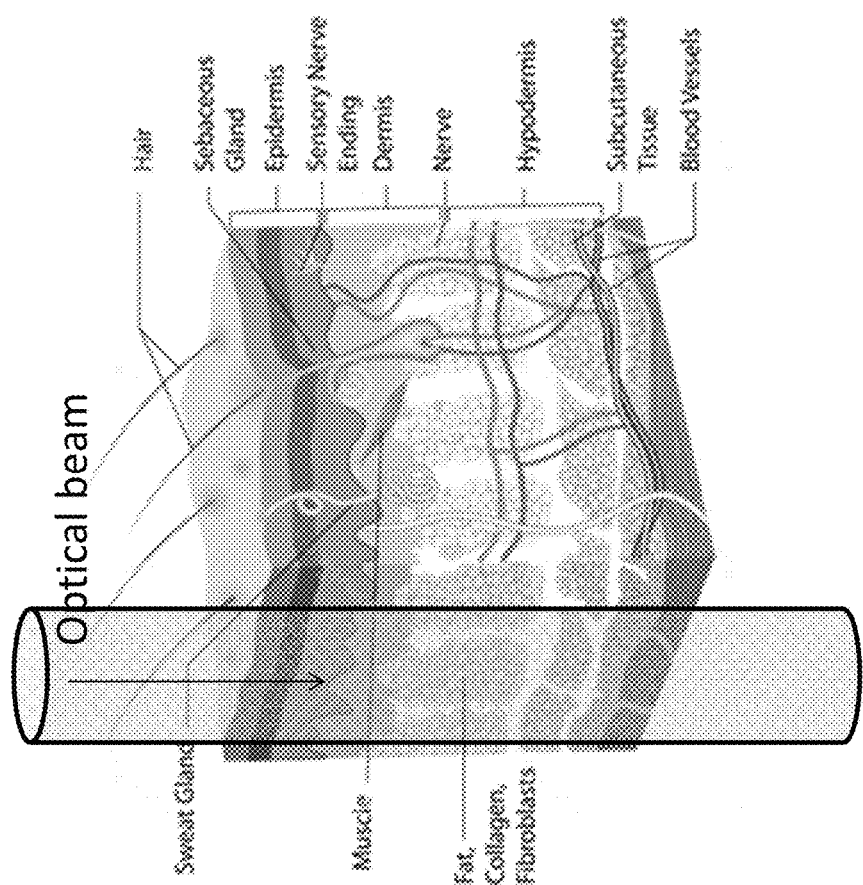
FIG. 3 illustrates that an optical beam goes through multiple layers before reaching blood vessels that are not proximate to the surface of an exposed body part.

FIG. 3 illustrates that an optical beam goes through multiple layers before reaching blood vessels that are not proximate to the surface of an exposed body part, for example, blood vessels at an earlobe area or tissue, e.g., flippers, between fingers. The network of blood vessels at these body parts is located underneath the epidermis, other layers of the skin, and other additional layers of tissue (e.g., muscle, fat, collagen, fibroblasts, etc.). According to such an embodiment, the optical beam would need to pass through multiple layers of tissue to reach the blood vessels. During the process, background noise from each of the multiple layers of tissue is introduced. Thus, measurements from blood vessels at these locations are not as accurate as measurement from blood vessels located close to the surface of an exposed body part, for example, the sclera and the backside of the eye lid. Such blood vessels are located in areas that do not have as many layers of tissue between the blood vessel and the surface of the body part, thereby minimizing background noise generated by intervening tissue layers. In some embodiments, areas adjacent to the blood vessel can also be scanned. The signals obtained from adjacent areas can be used to calibrate the signals obtained from the blood vessel, i.e., to subtract the effect of surface reflection and other background noise. In some embodiments, the temperature of the detected area may be monitored (e.g., by a temperature monitoring device) and used to calibrate the effect of the signals' dependence on temperature. The temperature monitoring device may communicate information associated with the temperature of the first area to a processing system, and the processing system may calibrate a concentration of the blood analyte based on the information associated with the temperature.

In various embodiments, the blood vessels scanned by device 100 are scanned in locations where there is no skin layer, e.g., the sclera. Such locations eliminate many layers of tissue that would otherwise be positioned between the blood vessels and device 100 during scanning at locations where there is a skin layer, e.g., ear lobe, between fingers, etc.

Analysis system 106 may be operable to perform various functions depending on the optical measurement approaches employed and the blood analyte of interest. For example, when the method uses polarization rotation to measure blood analyte concentrations, analysis system 106 is configured to determine analyte concentrations based on detected polarization changes associated with the analyte. When the OCT method is used, analysis system 106 is configured to determine analyte concentrations based on detected interferometric signals associated with the analyte. When Raman spectroscopy is used, analysis system 106 is configured to determine analyte concentrations based on detected Raman spectrum associated with the analyte. When NIR or MIR is used, analysis system 106 is configured to determine analyte concentrations based on detected absorption coefficients associated with the analyte of interest.

Analysis system 106 includes processor 108, memory 110, program instructions 112, and one or more communication interfaces 114. It should be appreciated that analysis system 106 may include any other computing devices or systems in addition to the components depicted in FIG. 1. Analysis system 106 will be further discussed with regard to an embodiment shown in FIG. 6.

Processor 108 may include any processor type capable of executing program instructions 112 in order to perform the functions described herein or capable of performing the functions without accessing instructions. For example, processor 108 may be any general-purpose processor, specialized processing unit, or device containing processing elements. In some cases, multiple processing units may be connected and utilized in combination to perform the various functions of processor 108. Processor 108 may fulfill the functions described by applying hardware- or software-based logic functions including reading, writing, calculating and comparing stored data and received signals. Such functions and associated algorithms are well known to computer scientists and digital/analog electrical hardware engineers.

Memory 110 may be any available media that can be accessed by processor 108 and any other elements in device 100. By way of example, memory 110 may include RAM, ROM, EPROM, EEPROM, CD-ROM or other optical disk storage, magnetic disk storage, or other magnetic storage devices, or any other medium that can be used to carry or store desired program code in the form of program instructions or data structures, and which can be executed by a processor. When information is transferred or provided over a network or another communications connection (either hardwired, wireless, or a combination of hardwired or wireless) to a machine, the machine properly views the connection as a computer-readable medium (CRM) or stored data structure. Thus, any such connection to a computing device or processor is included in memory 110. Combinations of the above are also included within the scope of computer-readable media.

Program instructions 112 may include, for example, executable code and data capable of causing a processing unit, a general-purpose computer, a special-purpose computer, special-purpose processing machines, or server system to perform a certain function or group of functions. In addition to program instructions 112, memory 110 may store any type of data of protocols necessary for achieving the functions described herein.

Communication interfaces 114 may include, for example, wireless chipsets, antennas, wired ports, signal converters, communication protocols, and other hardware and software for interfacing with external systems. For example, system 100 may receive data via communication interfaces 114 from remote data sources (e.g., remote servers, internet locations, intranet locations, wireless data networks, etc.) or from local media sources (e.g., external drives, memory cards, specialized input systems, wired port connections, wireless terminals, etc.). As another example, system 100 may receive user-input and user-commands via communication interfaces 114 such as, for instance, wireless/remote control signals, touch-screen input, actuation of buttons/switches, voice input, and/or other user-interface elements. Communication interfaces may also be used to output graphical user interfaces and processing results.

FIGS. 4 and 5 show example systems that include optical coherence tomography (OCT) system components in accordance with various illustrative embodiments. It should be appreciated that the OCT system is one of the non-invasive optical system that can be used in accordance with the disclosure. Other system, such as polarization rotation system, Raman spectroscopy system, NIR system, and MIR system can also be used, as also made clear elsewhere in the specification.

As shown in system 400 in FIG. 4, light (shown by the dashed line) is emitted from a light source 402, through an OCT interferometer 408, and to an area 414 by action of a moveable mirror 412, through a collimating lens 416. Although a moveable mirror is one way to implement a method in which the position of the illuminated spot is tunable, other control methods may be used to accomplish this feature. For example, acousto-optical deflectors, a movable light source, movable lenses, contractible lenses, or electro-optical deflectors could be used instead of a moveable mirrors in an example embodiment.

System 400 also includes a first detector 404 configured to detect light reflecting from or transmitting through area 414. System 400 also includes an analysis system 406 that is configured to analyze the detected light characteristics and perform additional functions as described hereinafter. As shown in FIG. 4, some embodiments that include an OCT device may use a second detector 410 to measure the light from the OCT interferometer 408.

As shown, area 414 may include two areas of interest (labeled "A" and "B" in FIG. 4). At different angles of moveable mirror 412, the light is directed to either area A (in which there is a blood vessel) or area B (in which there is no blood vessel). Area 414 is on an exposed body part where bloods vessels are proximate to the surface of the exposed body part. In an embodiment, area 414 is on the sclera. In another embodiment, area 414 is on the backside of the eye lid. Area B is optional. In some embodiment, analyte concentrations may be determined from optical properties of area A alone. To ensure that a vessel is in the scanned tissue area, an operable depth may be prescribed for the device. Alternatively, the device may be programed to determine whether a blood vessel was detected in the scanned area and provide an alert to the user if the position is not satisfactory.

As shown in FIG. 5, system 500 includes a single detector 504 to receive both the OCT interferometry signals and the absorption profile signals. Light (shown by the dashed line) is emitted from a light source 502, through an OCT interferometer 508, and to an area 514 by action of a moveable mirror 512, through a collimating lens 516. Although a moveable mirror is one way to implement a method in which the position of the illuminated spot is tunable, other control methods may be used to accomplish this feature. For example, acousto-optical deflectors, a movable light source, movable lenses, contractible lenses, or electro-optical deflectors could be used instead of a moveable mirrors in an example embodiment. System 500 also includes a detector 504 configured to detect light reflecting from or transmitting through area 514. System 500 also includes an analysis system 506 that is configured to analyze the detected light characteristics and perform additional functions as described hereinafter. Area 514 is on an exposed body part where bloods vessels are proximate to the surface of the exposed body part. In an embodiment, area 514 is on the sclera. In another embodiment, area 514 is at the backside of the eye lid.

FIG. 8 shows associated signals that may result from the use of detector 500 from FIG. 5 in accordance with an illustrative embodiment. As shown in FIG. 8, incoming signals 800 include absorption-profile information modulating the interferometric signal for use in the OCT process. Additionally, FIG. 8 shows a possible result of the analysis system separating the two effects into a corresponding absorption profile 802 and an interferometric signal 804. Once separated, the signals may be processed as usual.

In some cases, a detection device may be designed to be kept on the patient continuously for a certain period of time. The detection device may therefore periodically monitor the analyte levels without needing to be actively supervised by the user. When a predetermined event in the analyte levels are detected, the device may alert the user and continue monitoring.

Example Methods

Figure 6:
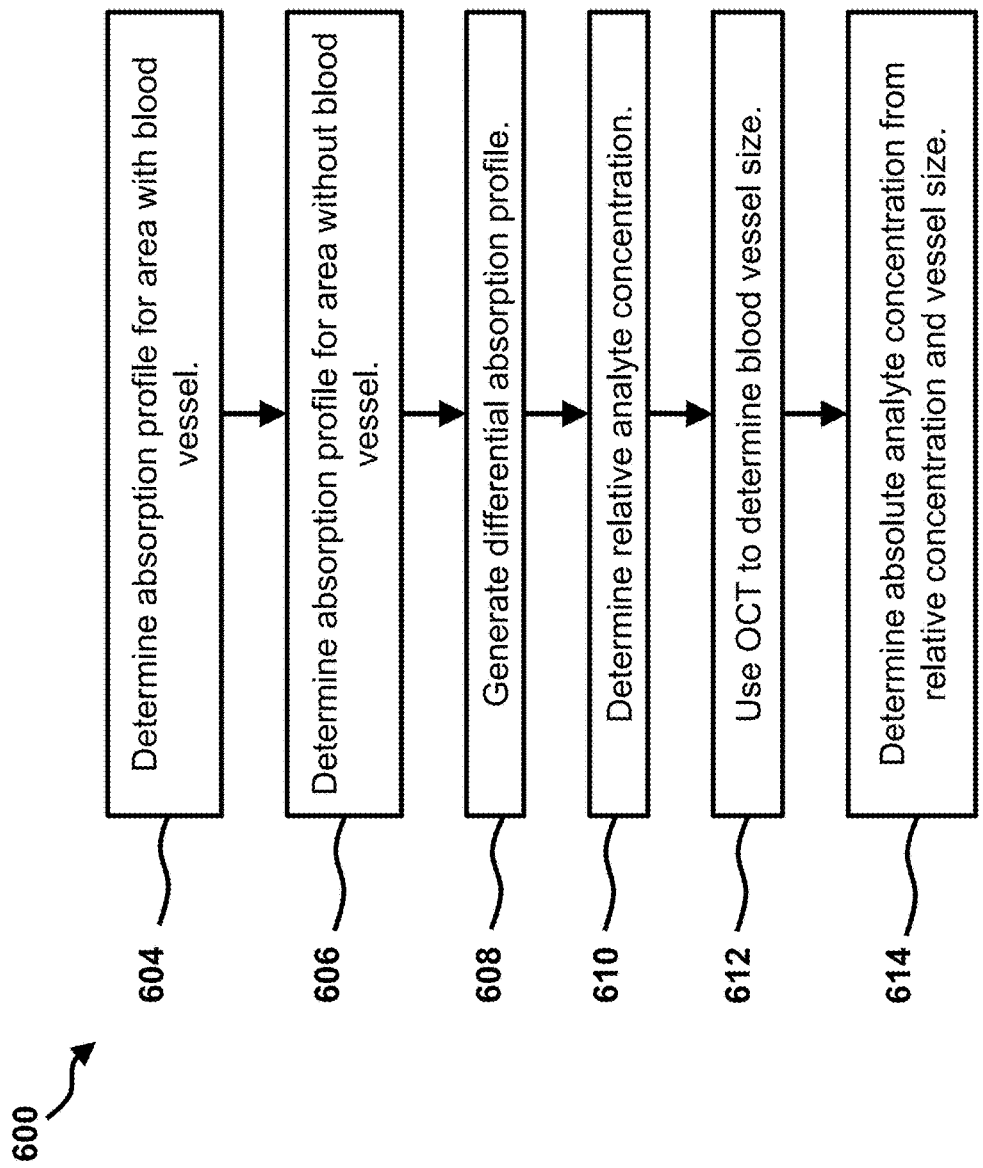
FIG. 6 is a flow chart illustrating an example method in accordance with an illustrative embodiment.

FIG. 6 is a flowchart illustrating method 600 according to an example embodiment, which may be performed by an example detection device or any device with capabilities consistent with the described operations. All of the methods described herein may include additional, fewer, or different operations than those shown, depending on the particular embodiment. Although FIG. 6 shows operations organized in a particular order, the illustrated order should not be seen as necessarily limiting. Rather, operations may be performed in any logical order, and some or all operations may be performed simultaneously with other operations. It should be appreciated that although the OCT approach is used in method 600, other approaches, such as polarization rotation, Raman spectroscopy method, NIR, and MIR method can also be used in accordance with the disclosure, as also made clear elsewhere in the specification.

As shown in operation 604, method 600 includes determining an absorption profile for an area that includes a blood vessel. Determining the light-absorption profiles of the area may be accomplished, in some embodiments, by illuminating the area and detecting light received from the illuminated area. As discussed above, the size and shape of the illuminated area may be dependent on the light source and other optical components in the detection device.

Method 600 may include operation 606, determining an absorption profile for an area that does not include a blood vessel. Operation 606 is optional. In some embodiments, the blood analyte concentration can be determined based on the absorption profile obtained from the area that includes a blood vessel alone. For example, the absorption profile can be compared to pre-determined absorption profiles with known blood analyte concentrations. In various embodiments, the detector may also illuminate and receive signals from areas other than the area with the blood vessel and the adjacent area without the blood vessel. In some example embodiments, the detection device may illuminate a path of tissue areas. In some cases, such a path may include substantially continuous sections of scanned areas.

As discussed above, the spectrum of the illumination may be tailored to penetrate the tissue to a desired level. Additionally, the spectrum may be tailored to include a particular wavelength that is associated with an analyte of interest. The analyte of interest may be, for example, hemoglobin, hematocrit, glucose, oxygen saturation, cholesterol, albumin, or bilirubin, among other example blood analytes. Each potential analyte of interest may be associated with a particular spectrum of absorption based on previous spectroscopy investigations. In some cases, the spectrum of absorption for particular analyte may include one or more peaks or notches around a single wavelength or set of wavelengths. Accordingly, the spectrum of the light source and detector may be selected to include the particular absorption wavelengths that are associated with the analyte of interest. In choosing the absorption wavelengths to investigate, the system may also compare the spectra of the analyte of interest to the absorption spectra of other analytes, blood constituents, or other tissue constituents that the light may encounter. Such a comparison may help to choose absorption wavelengths that would be less affected by the presence both relative concentrations of tissue materials other than the analyte of interest. In some cases, multiple absorption-profile characteristics of the analyte of interest may be investigated and the relative concentration determined. For example, the absorption characteristics at several frequencies may be included in a predictive statistical model with the value of each characteristic weighted according to the results of statistical testing. In an example embodiment, the detector need not determine, or be instructed, where the two areas of interest are located prior to performing the detection process. Rather, the positions of the two tissue areas may be designated following the illumination and collection of data. Indeed, the collected data may be used in selecting the positions of the areas to be compared. Therefore, the light source may be configured to illuminate (either simultaneously or in succession) various areas in a predetermined pattern.

A light detector, such as detectors 104, 404, 410, and 504 may be configured to detect light returning from the illuminated areas. Some light detectors may be implemented in a transmissive arrangement, in which the detector is positioned on an opposite side of the tissue area from the light source to detect light that passes through the tissue area and comes out in a same direction. Other detection systems may be implemented in a reflective arrangement, in which the detector is positioned on the same side of the tissue area as the light source to detect light that passes into the tissue area and reflects back from surrounding tissue or a reflective surface placed on the opposite side of the tissue area.

The result of the detection may be a profile of illumination intensity versus either time or wavelength/frequency. Since the location of the two tissue areas of interest may not be known at the beginning of the process, the resulting light detection data may include wavelength vs. time profiles for multiple tissue areas. The value for each tissue sample may be used to produce an average differential absorption profile. Alternatively, the values for each tissue sample may be combined with values for other blood vessel or non-blood-vessel tissue areas to produce the average differential absorption profile. In some cases, multiple blood vessels may be detected across an area of illumination, either before or after the illumination/detection process. In such a case, the detector may be programmed to determine the position of each blood vessel as well as positions in which no blood vessels are contained, so that concentration values from more than one blood vessel may be combined together to better approximate the concentration of the analyte of interest. In other cases, multiple positions along the same blood vessel may be measured and values associated with the multiple positions averaged to increase the precision of the determined concentration. As will be discussed, the size of the blood vessel(s) may be determined. If the results of multiple tissue areas are averaged together, the results may be weighted according to the relative size of the blood vessels. In other embodiments, the process may continue until a relative concentration of the blood analyte of interest is determined before averaging the results of several blood vessels or positions along a single blood vessel.

As shown in operation 608, method 600 may further include generating a differential light-absorption profile by comparing the light-absorption profile of the areas having the blood vessel to the light-absorption profile of the adjacent area not having the blood vessel. In the simplest case, such comparison may involve merely subtracting the absorption value at each wavelength of one profile from the corresponding absorption value in the other profile. In other cases, more advanced mathematical algorithms may be used. In the case of multiple sets of tissue areas, the system may generate a differential absorption profile for each set of tissue areas. In some cases, an area may be used in more than one set to make up for a lack of either type of area (blood vessel or non-blood vessel). In other cases, the values for each type of area may be averaged prior to generating the differential absorption profile. In such an example, a single differential absorption profile may represent an averaged differential absorption profile.

FIG. 7 shows example spectra 702 that may be used in generating the differential profile along with the resulting differential profile vs. wavelength 704 or time 706 (for a particular wavelength of interest). In this example, position A is the tissue area that includes the blood vessel and position B is the tissue area that does not include the blood vessel.

As shown at operation 610, method 600 may further include using the differential absorption profile to determine a relative analyte concentration. The relative concentration may be evaluated based on the relative amount of absorption in the area containing the blood vessel. If the light absorption is higher (relative to some normal absorption value) at the wavelengths associated with the analyte of interest, then the concentration may be judged to be higher than normal. In some embodiments, the detection device may store a normal absorption profile for a user of the device, so that the received detection data may be compared to the normal values for the user. In other cases, the differential absorption profile may be compared to a template profile that is preprogrammed in the system. In either case, the stored profile may be fine-tuned each time that the device is used to better approximate a normal value of absorption for the user at the wavelengths of interest.

In some cases, a device may detect the blood analyte concentration based on the relative absorption of wavelengths of light that the blood analyte either absorbs or reflects. For example, if the blood analyte heavily absorbs light with wavelengths close to 1140 nm and close to 960 nm, then a system may measure the amount of absorption at those wavelengths and relate the absorption directly to the concentration of the analyte.

In other cases, a device may detect the blood analyte concentration based on the relative absorption of wavelengths of light that other blood constituents absorb or reflect. For example, if blood without the analyte of interest absorbs 1075 nm wavelength light, then a system may measure the amount of absorption at 1075 nm and relate the absorption inversely to the concentration of the analyte. Such a technique is based on the fact that increases in the concentration of one analyte can cause decreases in the concentration of other constituents.

In some cases, a system may combine the relative increases in light-absorption in the wavelengths associated with absorption by the analyte of interest with the relative decreases in the light-absorption in the wavelengths associated with absorption by other blood constituents to find an overall concentration level. As a particular example, a system may be used to study glucose concentration in blood by taking the relative increases in absorption near 960 nm and 1140 nm wavelength (where light absorption has local peaks for glucose) and subtract the relative decrease in absorption near 1075 nm wavelength (where light absorption has a local peak for water). In this way, the effect of glucose concentration on the light-absorption spectrum of water, which may be the most significant constituent in blood, may be monitored.

In order to determine an absorption profile for the scanned tissue areas, the analysis system, or the detector itself, may be configured to receive or access information regarding the emission spectra of the light source, the reflection/transmission spectrum of various tissue components, or the results of previous scans in order to compare the scans to the currently received light-absorption profiles. However, such pre-existing data may not be required, since the system may use only the differential spectra for determining the relative concentration of the analyte of interest.

As shown at operation 612, method 600 may also include using an OCT system to determine blood vessel size. In other embodiments, this operation may be omitted. Additionally or alternatively, an OCT system may be used to determine a number of different characteristics of the blood vessels. For example, OCT may be used to determine the position of the vessels, determine the speed of blood flow in the vessels, and determine the number of vessels in a giver tissue area.

The OCT system may detect the presence and characteristics of a blood vessel according to systems described in other disclosures by the present inventor. FIG. 9 shows an example image 900 obtained through an OCT system along with a corresponding model 902 for the blood vessel images in image 900 in accordance with an illustrative embodiment. As shown, the detected blood vessel may be modeled by an idealized ellipse with a detected width 904 and height 906. The relative analyte concentration detected may then be normalized according to the detected size. For example, larger blood vessels may have higher absorption levels associated with all blood constituents. Accordingly, to compare a concentration reading from a larger blood vessel to a normal value taken from a smaller blood vessel, the absorption (or corresponding concentration) level must be reduced prior to comparison. In some embodiments, multiple known levels of concentration may be stored for comparison.

As shown at operation 614, method 600 may also include determining an absolute analyte concentration from the relative analyte concentration and the determined size of the blood vessel. In other embodiments, operation 614 may be omitted. In some example embodiments, both operations 612 and 614 may be omitted, and the relative analyte concentration may be returned as the result of the detection process. In embodiments that include operation 614, the absolute analyte concentration may be determined by normalizing the detected relative analyte concentration to the detected size and comparing the normalized concentration to one or more known concentrations. In other embodiments, a relation (e.g., a mathematical function, logical set of operators, statistical model, or decision tree) between relative analyte concentration, blood vessel size, and absolute analyte concentration may be stored on the device or a connected system and used to determine the absolute concentration.

Such a relation may be determined by the system, and may be specific to a user, analyte, device, or diagnosis. Some devices/systems may store multiple relations according to the users, analytes, etc. with which it is used. For example, the relationship between relative and absolute analyte concentration may be found through in-vitro testing. As a particular implementation of in vitro testing, liquids containing known absolute analyte compositions may be run through artificial blood vessels (rubber, glass, synthetic plastic, or natural fiber tubes) of various sizes and scanned with the detector to determine the relationship between relative and absolute analyte amounts for different sized vessels. Alternatively, the results from a detector's in vivo scanning of blood vessels of varying sizes may be compared to results of other blood tests run on blood from the same vessels. In some cases, the user may scan their own blood vessels, run additional analysis on their blood (such as a finger prick test) and provide the results of the additional analysis to the device. In this way, the device may calibrate its formulas for determining absolute analyte concentration for the particular user. In addition to blood vessels, a sophisticated OCT system may be capable of detecting blood flow (by measuring the Doppler Effect in the blood vessel). An analysis module may use this information to further normalize the concentration value of the tested vessel to the known-concentration spectrum/spectra.

In some cases, analyte concentration may be related to the blood flow. For example, an increased concentration of particular analytes (e.g., glucose) may increase the speed (perfusion) of blood flow through a blood vessel. Accordingly, the detection device may track the perfusion of blood in a vessel and use the perfusion as an indicator of analyte concentration. In particular, the relative perfusion may be tested and compared in any of the manners as described above with respect to analyzing the relative light absorption of the vessel. In one embodiment, therefore, a system may use only the speed of blood flow to estimate a concentration of some analytes. In other embodiments, the perfusion may be analyzed and combined with the light-absorption results in order to increase the accuracy or precision of an analyte concentration estimate. Any weighting functions may be applied in combining the concentration determined by perfusion with the concentration determined by light-absorption.

Figure 10:
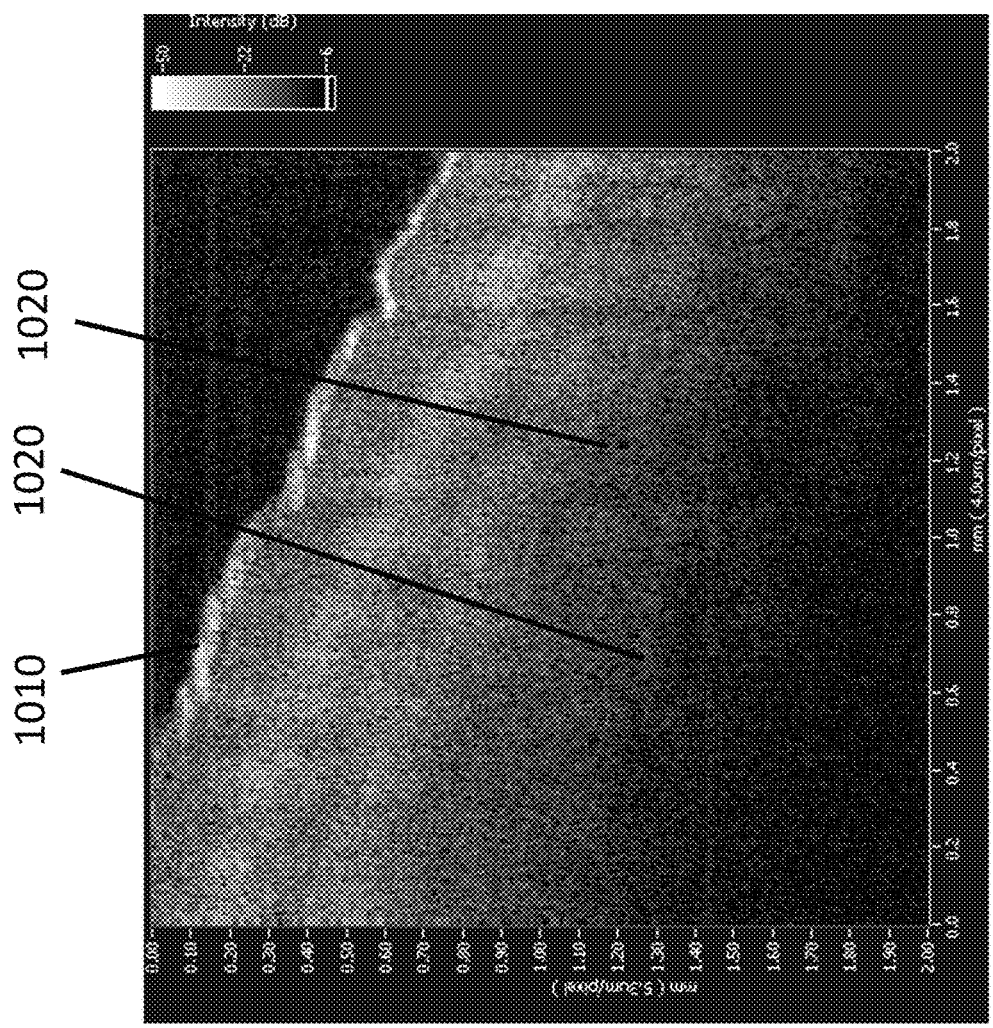
FIG. 10 is a measured OCT image of blood vessels at a fingertip in accordance with an illustrative embodiment.
Figure 11:
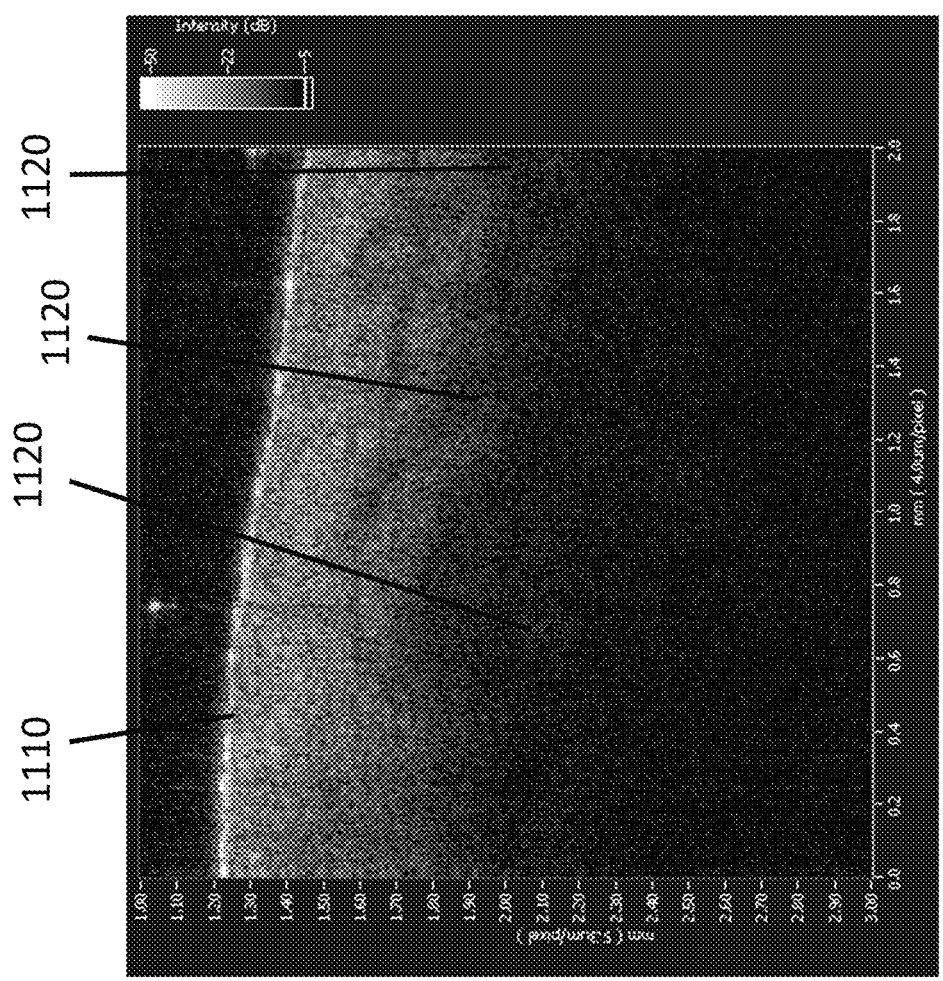
FIG. 11 is a measured OCT image of blood vessels at an ear lobe in accordance with an illustrative embodiment.
Figure 12A:
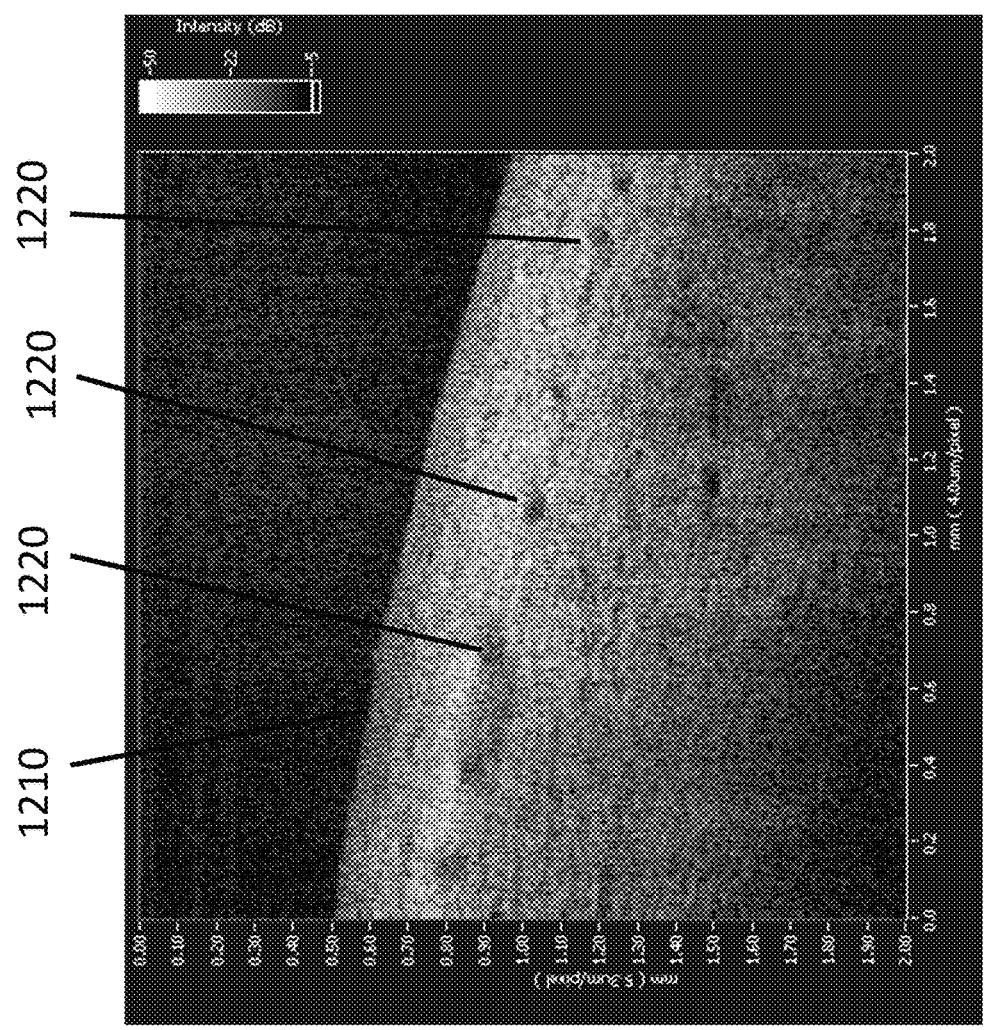
FIGS. 12A and 12B are measured OCT images of blood vessels on a sclera of an eye in accordance with an illustrative embodiment.
Figure 12B:
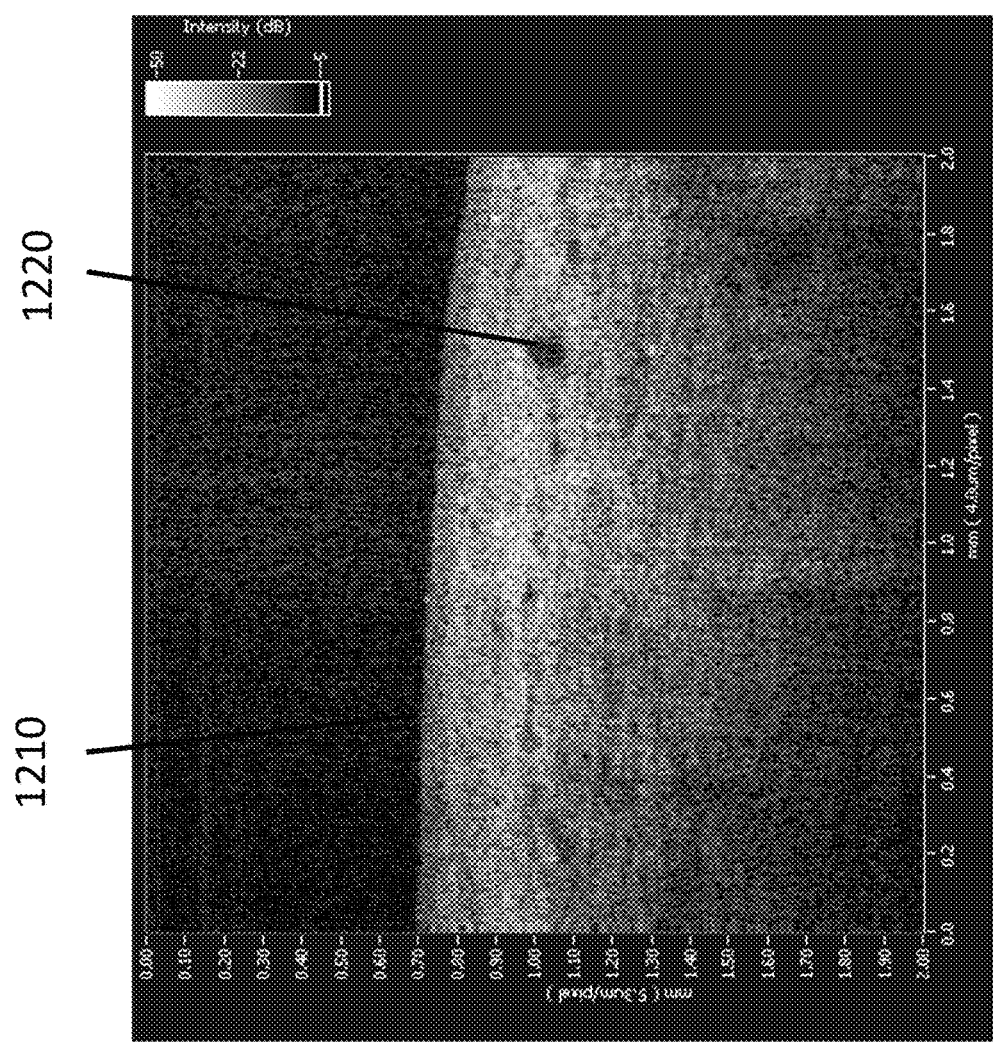
Figure 13:
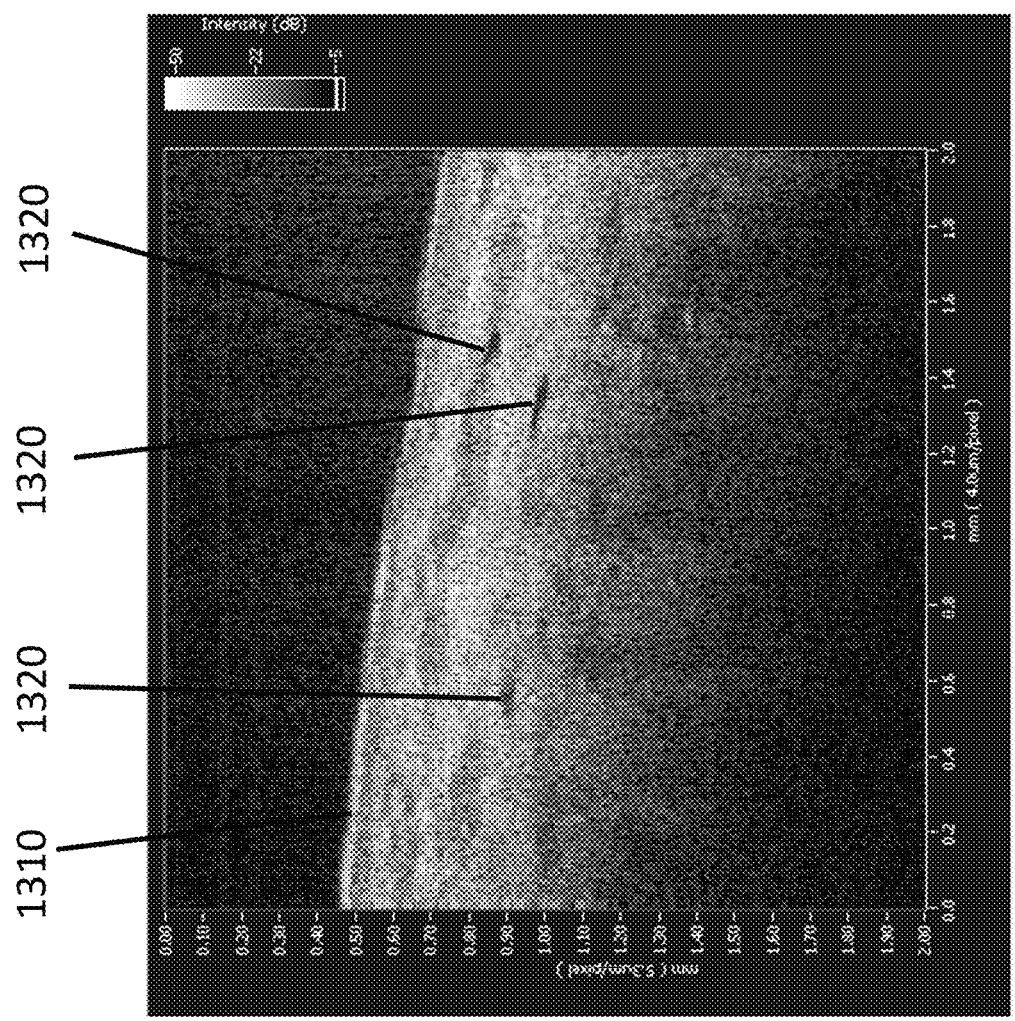
FIG. 13 is a measured OCT image of blood vessels on a backside of an eyelid in accordance with an illustrative embodiment.

FIGS. 10-13 are measured OCT images of blood vessels at different parts of the body. Specifically, FIG. 10 is an OCT image of blood vessels 1020 at a fingertip. FIG. 11 is an OCT image of blood vessels 1120 at an ear lobe. FIGS. 12A and 12B are OCT images of blood vessels 1220 on a sclera of an eye. FIG. 13 is an OCT image of blood vessels 1320 on the backside of an eyelid.

As shown in FIG. 10, blood vessels 1020 at the fingertip are more than 1 millimeter (mm) below surface 1010. Signals from blood vessels 1020 at the fingertip were faint, being embedded in noise due to tissue scattering, and interference of sweat glands and other lipids and shadows of hairs. As shown in FIG. 11, blood vessels 1120 are positioned a distance below surface 1110, and thus the signals of blood vessels 1120 at the ear lobe were also faint. In addition, it was hard to capture the structure of a tissue that primarily consists of capillary blood vessels because of their small dimensions. Typically, the dimension of a capillary blood vessel is about 3 microns to about 10 microns.

On the other hand, OCT images measured at the sclera and the backside of an eyelid in accordance with some embodiments showed stronger signals. Clearer images of blood vessels 1220, 1320 were obtained as shown in FIGS. 12 and 13 because blood vessels at these body parts are located closer to the surface 1210, 1310 of the body part. Typically, blood vessels at the sclera and the backside of an eyelid are located less than about 0.1 millimeter (mm) to about 0.5 mm deep under the surface. Interferences from surrounding tissues are also minimized because melanin, epidermis, hair, etc. are not present at these body parts.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments.

What is claimed is:

1. A method comprising:
   receiving, by a processing system from a light detector, information associated with first optical signals detected by the light detector, wherein the first optical signals are detected from a first area illuminated by a light source, wherein the first area includes a blood vessel, and wherein the blood vessel is proximate to a surface of an exposed body part; and
   determining, by the processing system, a concentration of a blood analyte based on the received information associated with the first optical signals, wherein determining the concentration of the blood analyte comprises:
      determining a first light absorption profile from the information associated with the first optical signals detected by the light detector from an area including the blood vessel;
      detecting a size of the blood vessel;
      comparing the first light absorption profile to a plurality of pre-determined light absorption profiles having known blood analyte concentrations; and
      calibrating a determined relative analyte concentration based on the size of the blood vessel.

2. The method of claim 1, wherein there is no skin layer between the blood vessel and the surface of the exposed body part at the first area.

3. The method of claim 1, wherein the first area is on an eye.

4. The method of claim 1, wherein the exposed body part is a sclera of an eye.

5. The method of claim 1, wherein the exposed body part is a backside of an eye lid.

6. The method of claim 1, wherein the blood analyte is one of glucose or oxidized hemoglobin.

7. The method of claim 1, wherein determining the concentration of the blood analyte further comprises:
   determining, from the information associated with the first optical signals detected by the light detector, a second light absorption profile for an area not having the blood vessel;
   generating a differential light absorption profile based on differences between the first light absorption profile and the second light absorption profile; and
   determining the concentration of the blood analyte based on the differential light absorption profile.

8. The method of claim 1, further comprising:
   receiving, by the processing system, from the light detector, information associated with second optical signals detected by the light detector, wherein the second optical signals are detected from a second area illuminated by the light source, wherein the second area is adjacent to the first area, and wherein the second area does not include a blood vessel; and
   calibrating, by the processing system, the concentration of the blood analyte based on the received information associated with the second optical signals.

9. The method of claim 1, further comprising:
   receiving, by the processing system, from a temperature monitor, information associated with a temperature of the first area detected by the temperature monitor; and
   calibrating, by the processing system, the concentration of the blood analyte based on the information associated with the temperature.

10. The method of claim 1, wherein the information associated with the first optical signals comprises polarization rotation, Raman spectrum, optical coherence tomography, near infrared spectrum, or mid-infrared spectrum.

11. The method of claim 1, wherein the blood vessel at the first area is located less than 0.5 millimeter deep under the surface of the exposed body part.

12. A non-invasive analyte detection device comprising:
   a light source configured to illuminate a first area, wherein the first area includes a blood vessel, and wherein the blood vessel is proximate to a surface of an exposed body part;
   a light detector configured to detect first optical signals from the first area; and
   a processor configured to:
      receive information associated with the first optical signals;
      determine a first light absorption profile from the received information associated with the first optical signals
      determine a size of the blood vessel; and
      determine a concentration of a blood analyte based on the first light absorption profile and the size of the blood vessel.

13. The device of claim 12, wherein the exposed body part is a sclera of an eye.

14. The device of claim 12, wherein the exposed body part is a backside of an eye lid.

15. The device of claim 12, wherein the blood analyte is glucose.

16. The device of claim 12, wherein the blood analyte is oxidized hemoglobin.

17. The device of claim 12, wherein:
   the light source is further configured to illuminate a second area, wherein the second area is adjacent to the first area, and wherein the second area does not include a blood vessel;
   the light detector is further configured to detect second optical signals from the second area; and
   the processor is further configured to:
      receive information associated with the second optical signals;
      create a second light absorption profile based on the received second optical signals;
      calibrate the concentration of the blood analyte based on the second light absorption profile.

18. The device of claim 12, further comprising a temperature monitor configured to detect a temperature of the first area, wherein the processor is further configured to receive information associated with the detected temperature from the temperature monitor and to calibrate the concentration of the blood analyte based on the information associated with the temperature.

19. The device of claim 12, wherein the information associated with the first optical signals comprises polarization rotation, Raman spectrum, optical coherence tomography, near infrared spectrum, or mid-infrared spectrum.

* * * * *